(12) United States Patent
Finklestein (10) Patent No.: US 9,023,001 B2
(45) Date of Patent: May 5, 2015

(54) SYSTEMS AND METHODS FOR PROVIDING A DEBRIDING WOUND VACUUM

(75) Inventor: Jerome L. Finklestein, Maspeth, NY (US)

(73) Assignee: Heal-Ex, LLC, Brooklyn, NY (US)

( * ) Notice: Subject to any disclaimer, the term of this patent is extended or adjusted under 35 U.S.C. 154(b) by 652 days.

(21) Appl. No.: 11/853,929

(22) Filed: Sep. 12, 2007

(65) Prior Publication Data

US 2009/0069760 A1    Mar. 12, 2009

(51) Int. Cl.
    *A61F 13/00*    (2006.01)
    *A61F 13/02*    (2006.01)
    *A61M 1/00*     (2006.01)

(52) U.S. Cl.
    CPC ..... *A61F 13/023* (2013.01); *A61F 2013/00174* (2013.01); *A61F 2013/00536* (2013.01); *A61F 2013/0054* (2013.01); *A61F 2013/00927* (2013.01); *A61M 1/0088* (2013.01)

(58) Field of Classification Search
    USPC ......... 604/305, 304, 307, 313, 317, 319, 540, 604/543; 606/27, 2, 3, 9; 602/43
    See application file for complete search history.

(56) References Cited

U.S. PATENT DOCUMENTS

| | | |
|---|---|---|
| 4,969,880 A | 11/1990 | Zamierowski |
| 5,100,396 A | 3/1992 | Zamierowski |
| 5,261,893 A | 11/1993 | Zamierowski |
| 5,527,293 A | 6/1996 | Zamierowski |
| 5,636,643 A | 6/1997 | Argenta et al. |
| 5,645,081 A | 7/1997 | Argenta et al. |
| 6,117,111 A | 9/2000 | Fleischmann |
| 6,142,982 A | 11/2000 | Hunt et al. |
| 6,345,623 B1 | 2/2002 | Heaton et al. |
| 6,398,767 B1 | 6/2002 | Fleischmann |
| 6,458,109 B1 | 10/2002 | Henley et al. |
| 6,553,998 B2 | 4/2003 | Heaton et al. |
| 6,685,681 B2 | 2/2004 | Lockwood et al. |
| 6,814,079 B2 | 11/2004 | Heaton et al. |
| 6,994,702 B1 | 2/2006 | Johnson |
| 7,004,915 B2 | 2/2006 | Boynton et al. |
| 7,216,651 B2 | 5/2007 | Argenta et al. |
| 7,338,482 B2 | 3/2008 | Lockwood et al. |
| 7,951,100 B2 | 5/2011 | Hunt et al. |
| 8,152,785 B2 | 4/2012 | Vitaris |
| 8,168,848 B2 | 5/2012 | Lockwood et al. |

(Continued)

OTHER PUBLICATIONS

International Search Report for International Application No. PCT/US08/75748 dated Nov. 10, 2008 (2 pages).

(Continued)

*Primary Examiner* — Tatyana Zalukaeva
*Assistant Examiner* — Benedict L Hanrahan
(74) *Attorney, Agent, or Firm* — Weiss & Arons LLP (57) ABSTRACT

Thus, systems and methods for a debriding wound vacuum may include a sponge for application to a wound, a flexible sheet for covering and sealing the wound, and a bladder. The bladder may be in fluid communication with at least a portion of the sponge. The bladder preferably contains a debridement substance. A negative pressure device may form part of the system and may be used to apply negative pressure via a hollow tube to the sponge. The negative pressure device may be adapted to apply negative pressure to the sponge via the hollow tube in order form a seal between the flexible sheet and the wound. The systems may also include microelectronic mechanical valves for releasing the debridement substance from the bladder.

13 Claims, 10 Drawing Sheets

(56) References Cited

U.S. PATENT DOCUMENTS

| | | |
|---|---|---|
| 8,187,210 B2 | 5/2012 | Hunt et al. |
| 8,188,331 B2 | 5/2012 | Barta et al. |
| 8,202,261 B2 | 6/2012 | Kazala, Jr. et al. |
| 2002/0150720 A1 | 10/2002 | Howard et al. |
| 2006/0173253 A1 | 8/2006 | Ganapathy et al. |
| 2007/0032755 A1 | 2/2007 | Walsh |
| 2007/0167926 A1 | 7/2007 | Blott et al. |
| 2007/0292489 A1* | 12/2007 | Bassiri et al. .......... 424/445 |
| 2011/0144599 A1 | 6/2011 | Croizat et al. |
| 2011/0172612 A1 | 7/2011 | Greener et al. |
| 2011/0196278 A1 | 8/2011 | Svedman et al. |
| 2012/0041403 A1 | 2/2012 | Bennett et al. |

OTHER PUBLICATIONS

V.A.C. Instill (2005).

* cited by examiner

SYSTEMS AND METHODS FOR PROVIDING A DEBRIDING WOUND VACUUM

FIELD OF TECHNOLOGY

The present invention relates to an apparatus and method for treating a wound by applying reduced pressure to the wound. Aspects of the disclosure relate more particularly to a wound vacuum. More specifically, aspects of the disclosure relate to systems and methods for promoting advanced wound care using a wound vacuum.

BACKGROUND OF THE INVENTION

The treatment of open wounds has long been a difficult area of medical practice. Closure of an open wound requires inward migration of surrounding tissue. Some wounds, however, are sufficiently large or infected that they are difficult to heal spontaneously. In such instances, the flow of blood to the epithelial and subcutaneous tissue may be restricted such that an edema—swelling of the body's tissues—forms near the surface of the wound. In the absence of sufficient blood flow, the wound is often unable to successfully fight infection and is unable to close.

Additionally, a wound may include dead tissue that remains attached to the wound, thereby preventing proper wound closure.

In certain circumstances, wounds are treated with a vacuum-assisted wound closure system that allows the wounds to heal more rapidly. Debridement of a wound—the surgical, chemical, mechanical, or autolytic (using the body's own processes) removal of wound tissue to promote healing—is typically performed prior to the use of a vacuum-assisted wound closure system in order to advance the process of cleaning dead and contaminated material from the wound. Nevertheless, because of a number of considerations, debridement is not always properly performed prior to the use of a vacuum-assisted wound closure system. Using the vacuum-assisted wound closure system in the absence of preceding optimal debridement may obtain sub-optimal results.

In one specific circumstance of negative side-effects obtained by lack of debridement, the dead tissue around a wound may promote ischemia of the live tissue still within the wound area. In certain situations, the ischemia may lead to progressive deterioration of wounds.

Such a phenomena may occur with partial thickness wounds. A partial thickness wound may include cell death that does not extend below the deepest epidermal structures. The ability to control or diminish the depth of wounds greatly enhances the prognosis for wound patients. Furthermore, this ability decreases morbidity resulting from such wounds.

Partial thickness wounds are formed from a zone of coagulation. The zone of coagulation may encompass tissue killed by the injury that caused the wound. The partial thickness wounds may also incorporate a zone of stasis. The zone of stasis is a layer of tissue immediately beneath the zone of coagulation.

While cells within the zone of stasis are viable, nevertheless, the blood flow is static because of collapse of surrounding and intrinsic vascular structures. Localized edema may play a part in such a collapse of local vascular structures. One important factor in maintaining the viability of the cells located in the zone of stasis is re-establishing blood flow within the zone of stasis soon after injury. Accordingly, it is further desirable to provide a technique for treating wounds by enhancing blood circulation to the wounded tissue to inhibit wound penetration.

It therefore also becomes desirable to provide an apparatus and method that may be adapted to advance the use of a vacuum-assisted wound closure system that simplifies and assures that proper debridement takes place prior to the use of the vacuum.

SUMMARY OF THE INVENTION

Systems and methods according to the invention may include a sponge for use with a wound vacuum comprising. The sponge may include either in a chamber located therein, or be impregnated therewith, a debridement substance. The debridement substance may be embedded in the sponge such that contact with fluid causes release of the debridement substance over a predetermined time period. Furthermore, the debridement substance may be released only after a certain predetermined time period. In certain embodiments, the time period for release may be based on the contact of the sponge with a liquid.

Accordingly, the present invention relates to a modified vacuum-assisted wound closure system adapted for concurrent applications of a tissue-digestive enzyme or other suitable tissue-digestive material and negative pressure. It should be noted that references herein to a tissue-digestive enzyme may be understood to include enzymes such as collagenase or other suitable tissue-digestive enzymes and/or other substances.

In certain embodiments of the invention, phototherapy may also be incorporated together with the implementation of the tissue-digestive enzyme.

Modified vacuum-assisted closure systems and methods according to the invention—which may include a foam pad for insertion substantially into the wound site and a wound drape for sealing enclosure of the foam pad at the wound site—may be modified to include systems and methods for introduction to the wound of a tissue-digestive enzyme. The systems and methods according to the invention may further include an optical light provider, whereby a desired wavelength of light may be directed into and about the wound site. Although the foam pad is placed in fluid communication with a vacuum source for promotion of fluid drainage, as known in the art, the addition of the optical light provider is noninvasive to the known negative pressure therapy and requires no substantial modification thereof. Such systems and methods are described in U.S. patent application No. 6,994,702 which is hereby incorporated by reference herein in its entirety.

Other embodiments of the invention relate to using a hydrocolloid dressing when administering the tissue-digestive enzyme. In such a dressing the outer layer is typically water resistant, and the inner layer forms a moist healing environment. DuoDerm® made by Convatec, Ltd. of Deeside, United Kingdom, is one of the many hydrocolloid dressings available on the market today. In uses according to the invention, the DuoDerm® may actually be used to administer the tissue-digestive enzyme, as will be described in more detail below.

According to the preferred embodiment of the present invention, the foam pad preferably comprises a highly reticulated, open-cell polyurethane or polyether foam for good permeability of wound fluids while under suction, as previously known in the art.

Finally, many other features, objects and advantages of the present invention will be apparent to those of ordinary skill in the relevant arts, especially in light of the foregoing discussions and the following drawings and exemplary detailed description.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

In the following description of the various embodiments, reference is made to the accompanying drawings, which form a part hereof, and in which is shown by way of illustration various embodiments in which the invention may be practiced. It is to be understood that other embodiments may be utilized and structural and functional modifications may be made without departing from the scope and spirit of the present invention.

Figure 1:
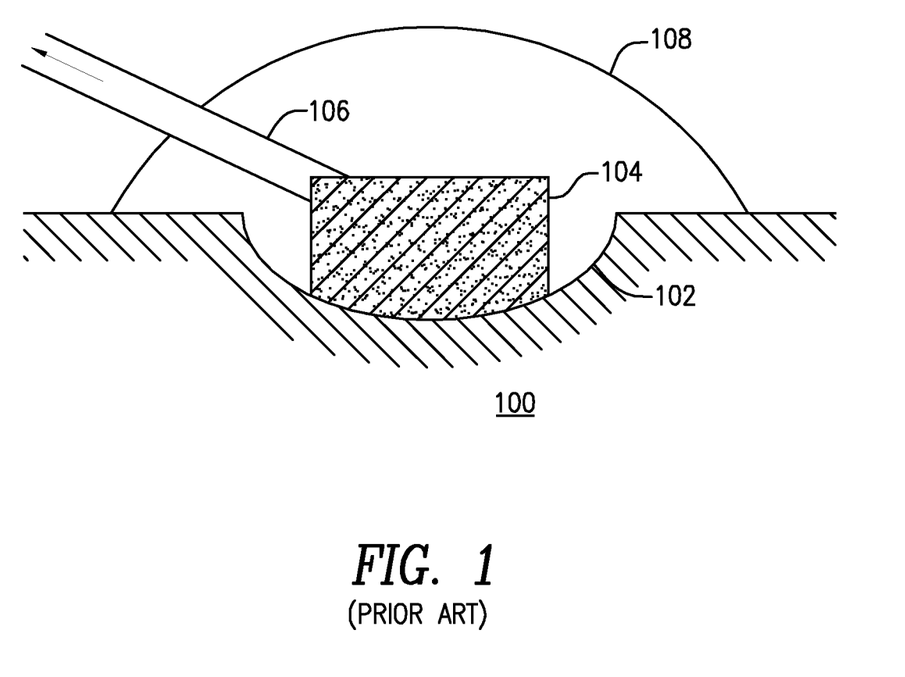
FIG. 1 shows a portion of a conventional negative pressure wound treatment device.

FIG. 1 shows a conventional wound treatment device 100 for treating wounds, such as wound 102, using negative pressure—i.e., below atmospheric pressure. A device as partially shown in FIG. 1 may preferably include a foam sponge 104 which may be formed from polyester or other suitable material. Preferably, the foam sponge may be in gaseous and/or fluid communication with a vacuum pump (not shown) via a hollow tube such as tube 106. Such a device may also be used concurrently with an adhesive sheet 108 which may be used to form a substantially gas-tight and/or fluid tight seal around the sponge such that the suction on the sponge via tube 106 may cause negative pressure to be built up within the sealed area—i.e., on and about the wound.

Such a negative pressure device, which is known in the art, may be used at negative pressures of about 125 millimeters Hg. The negative pressure device is typically used to promote healing of wounds. However, the use of such a device, which creates suction on the wound and stimulates tissue growth therein and blood flow thereto, typically requires the following steps when used with infected wounds or other more difficult wounds.

First, the wound may be desensitized using a known analgesic. Second, the wound may be treated with a preferably absorbable antibiotic to reduce the chance of infection, or to reduce an infection already present. Then, the wound may be debrided—i.e., the wound or burn tissue may be removed to promote healing of the healthy tissue. Thereafter, wound closure, either with sutures and/or skin grafts, may be implemented.

Alternatively, a negative pressure device, such as partially shown in FIG. 1, may be used together with the application of an analgesic, an antibiotic, and/or debridement. In this embodiment, negative pressure is first applied until a seal is formed, then, for the application of the analgesic, antibiotic, and/or debridement, the negative pressure is removed and the various treatments are applied.

If debridement is not performed together with the use of the negative pressure device, wound or burn tissue may remain lodged between exudate that is being suctioned from the wound and the dead tissue. This exudate may then remain trapped under the dead tissue. In such a circumstance, the use of the negative pressure device may provide only sub-optimal improvement to the condition of the wound.

More importantly, it may not be practical to debride every wound that is a candidate for negative pressure. Yet, many negative pressure devices are used in the absence of debridement and, accordingly, attain only sub-optimal results.

The invention, however, preferably deals with these complications involving negative pressure devices. The invention provides systems and methods for incorporating debridement vehicles within existing negative pressure wound healing devices. Accordingly, uses of devices according to the invention may allow for the more optimal implementations of negative pressure devices.

In order to better understand a first embodiment of the invention, it should be understood that certain known negative pressure devices may include a port for the introduction of analgesics and/or antibiotics into and about the wound area. In a first embodiment of the invention, a tissue-digestive enzyme such as collagenase or other suitable tissue-digestive material, may be introduced through such a port in the negative pressure device.

Figure 2:
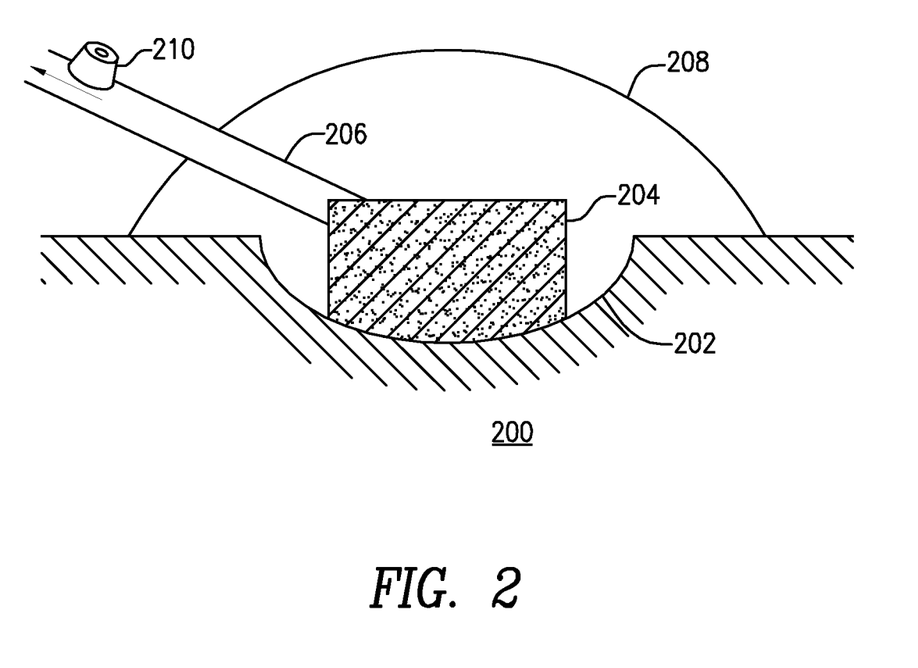
FIG. 2 shows a portion of another conventional wound treatment device.

FIG. 2 shows a negative pressure device 200 which is substantially similar to the negative pressure device shown and described in FIG. 1. The only difference between device 200 and device 100 is that device 200 incorporates a port 210 which may be used for the introduction of analgesics, antibiotics, and/or tissue-digestive enzymes. The numbered elements which are substantially the same between FIG. 1 and FIG. 2 have not been described again with respect to FIG. 2 for the sake of brevity.

In one embodiment of a method according to the invention, device 200 shown in FIG. 2 may be used according as follows. First, the negative pressure device is applied to the wound such that sheet 208 forms a seal about the wound. Once the seal has been formed, the negative pressure device may cease providing suction for a certain period of time—e.g., one hour—wherein an analgesic may be added to the wound via port 210. Then, the suction may be reapplied thus maintaining the seal about the wound. Some time after the application of the analgesic (or prior to the application of the analgesic), the suction may again be ceased and, while still in a sealed environment, an antibiotic may be introduced to the wound. This application of antibiotic may be maintained for a period of two hours or some other suitable time.

Thereafter, suction may be reapplied thus further maintaining the seal about the wound. Until this point of the method according to the invention, and for the following step, it is important to note that sheet 208 of the negative pressure device has been sealed to the wound, preferably about the wound's outer perimeter.

Finally, the suction may again be ceased, and a tissue digester such as collagenase may be introduced through port 210. The tissue digester may be allowed to sit on the wound for a time that is sufficient to substantially debride the wound. Thereafter, the suction can be reintroduced and the digested tissue may be taken up by tube 206 together with any exudates from the wound. In certain embodiments of the invention, tube 206 (as well as an uptake port from sponge 204) may be of relatively larger diameter tubes and uptake ports than tubes and uptake ports associated with a typical negative pressure device. For example, in certain embodiments of the invention the uptake port and tube may be ⅜ths of an inch in diameter, ½ an inch in diameter or even larger in order to accommodate the uptake of the digested wound or burn tissue together with the wound exudate.

Figure 3:
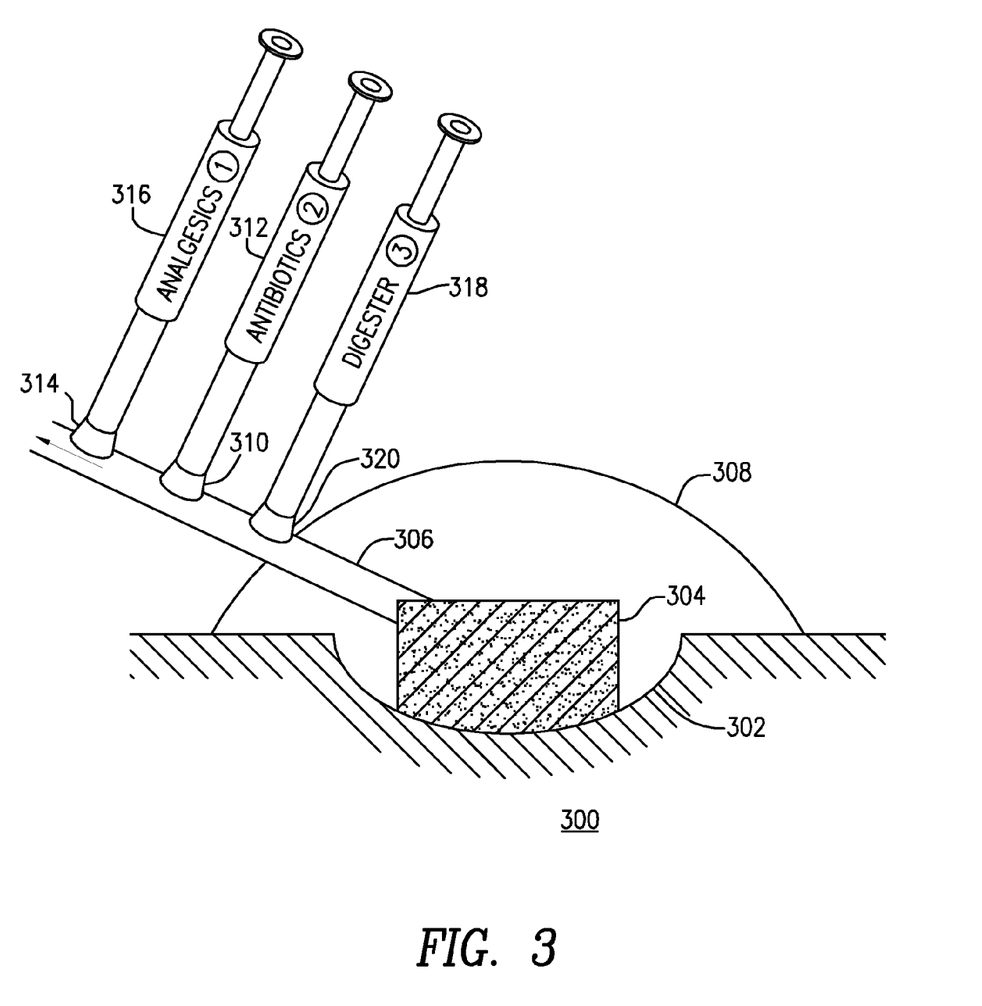
FIG. 3 shows a portion of a negative pressure wound treatment device according to the invention.

In one embodiment of the invention, shown in FIG. 3, multiple preferably pre-numbered, pre-loaded and pre-labeled ports 310, 314 and 320 and/or tubes 312, 316, and 318 may be used to allow for a user to efficiently and accurately introduce the appropriate substance into the wound in a timely and non-deleterious manner. In other embodiments of the invention, the time of application, such as two hours or four hours, can also be displayed on the pre-loaded ports.

In such an embodiment of the invention shown in FIG. 3, tubes 312, 316 and 318 may preferably be pre-filled with the appropriate substance and pre-labeled. Furthermore, application instructions—e.g., "cut off suction, apply this substance for two hours, and then reengage suction"—may also be provided on the labels of the tubes so a health care provider may be able to accurately apply the correct substance in a predetermined sequence.

In other embodiments of the invention, the analgesic, antibiotic and tissue digestive substances may be introduced through time release compartments in the sponge. FIGS. 4-7 shows various embodiments of a sponge that can be used in systems and methods according to the invention.

Figure 4:
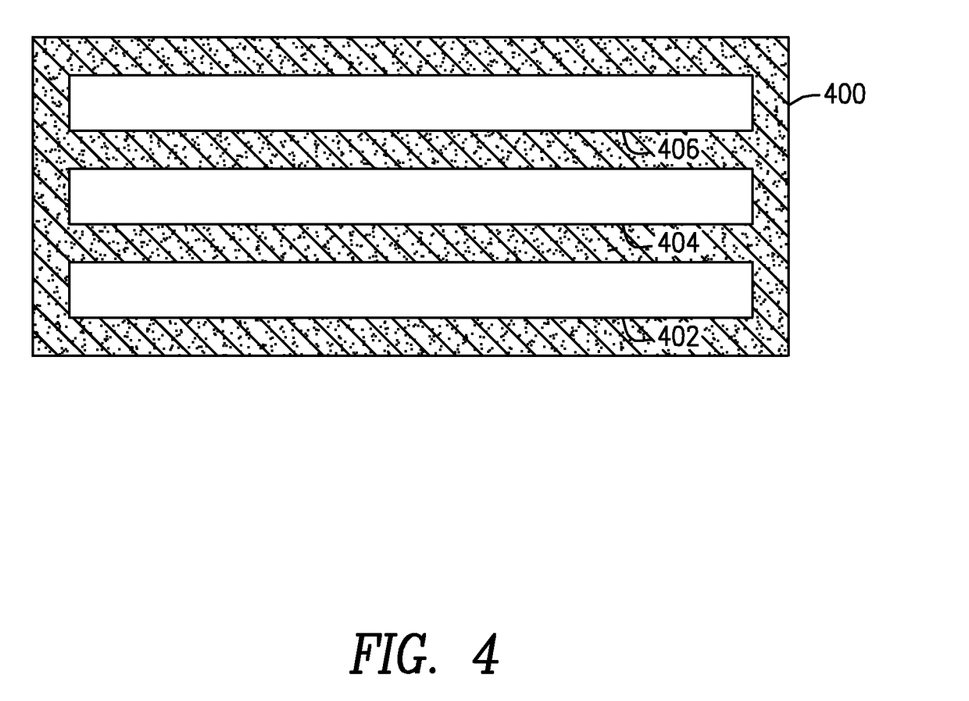
FIG. 4 shows a sectioned view of an embodiment of a sponge according to the invention.

FIG. 4 shows an first embodiment of a sponge 400 according to the invention. In such a sponge, chamber 402 may preferably be filled with an analgesic substance, chamber 404 may preferably be filled with an antibiotic substance 404, and chamber 406 may be filled with a tissue digestive substance. When using such a sponge 400, chambers 402, 404, and 406 may preferably be configured whereby each of the chambers preferably releases its respective contents at a predetermined time.

In one embodiment of the invention, a time line of release of the chambers may be as follows: For the first few minutes during and immediately following the implementation of a seal, preferably no contents are released in order to the assure formation of a good seal. Thereafter, first chamber 402 opens and the analgesic contents are released into the sponge (and, thereafter, dispersed throughout the wound). Then another predetermined time period passes, as the suction is preferably reapplied. Thereafter, second chamber 404 opens and the antibiotic contents are released into the sponge. Another predetermined time period passes, and the suction is applied once more. Finally, third chamber 406 opens and the tissue digestive enzyme is released.

Figure 5:
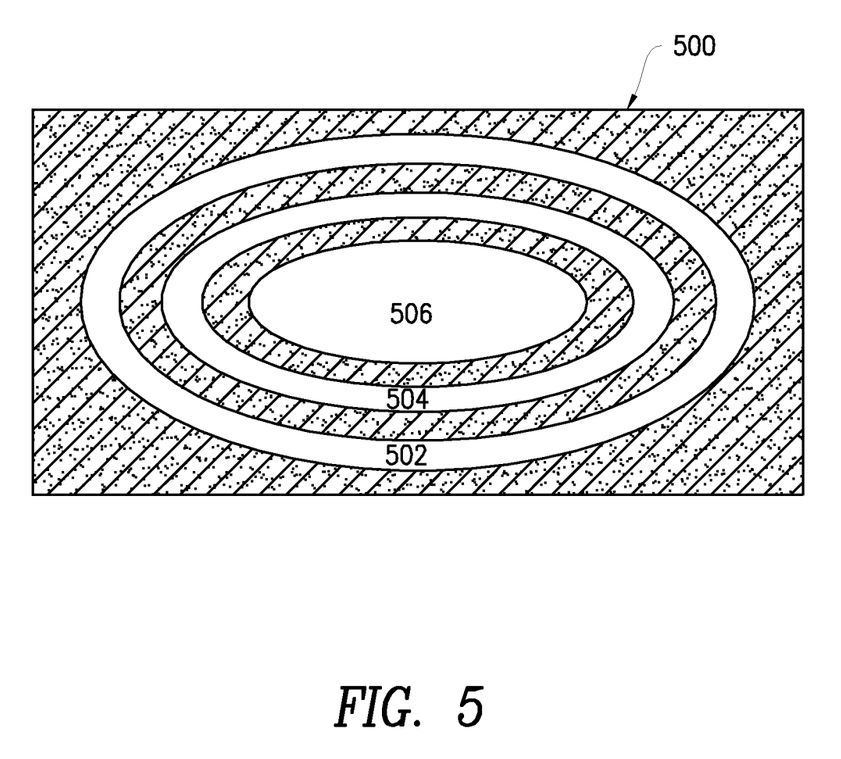
FIG. 5 shows another sectioned view of an embodiment of a sponge according to the invention.

FIG. 5 shows yet another embodiment of a sponge 500 according to the invention. FIG. 5 shows that sponge 500 may preferably include separate chambers 502, 504, and 506 that are formed in a concentric fashion. In fact, in this, or other embodiments, the sponge may contain chamber walls, or at least portions of chambers, that slowly dissolve and are taken up by the suction together with the exudate and the wound and/or burn tissue. In such embodiments, the amount of dissolvable sponge material may be used to gauge the timing of the release of the substances in the chambers.

In yet other embodiments of the invention, a camera may be installed in the sponge that allows the real-time uptake of optical information from the wound. In such an embodiment, the optical information relating to the wound may be used to accurately coordinate the amount of time that the tissue digestive substance is allowed to remain on the wound without suction. For example, if the health care provider introduced the tissue digester through a port in the negative pressure device, the initial debriding may only take 2-3 hours instead of 4 hours. In such circumstances, the camera could provide feedback to the health care provider that the debriding was no longer necessary and the suction could be reintroduced to the wound. This process could substantially reduce the amount of time before the negative pressure was introduced to the wound, thereby more quickly increasing blood flow to the wound, stimulating tissue growth, and reducing the healing time of the wound. Such a camera may be coupled either wirelessly or by wire to a viewable display external to the wound area.

It should be noted that optimal debriding may occur only after multiple applications of tissue digestive enzyme. Accordingly, the disclosure herein in each of the embodiments of the invention, may include multiple applications of tissue digestive enzyme according to the sequences set forth herein.

Figure 6:
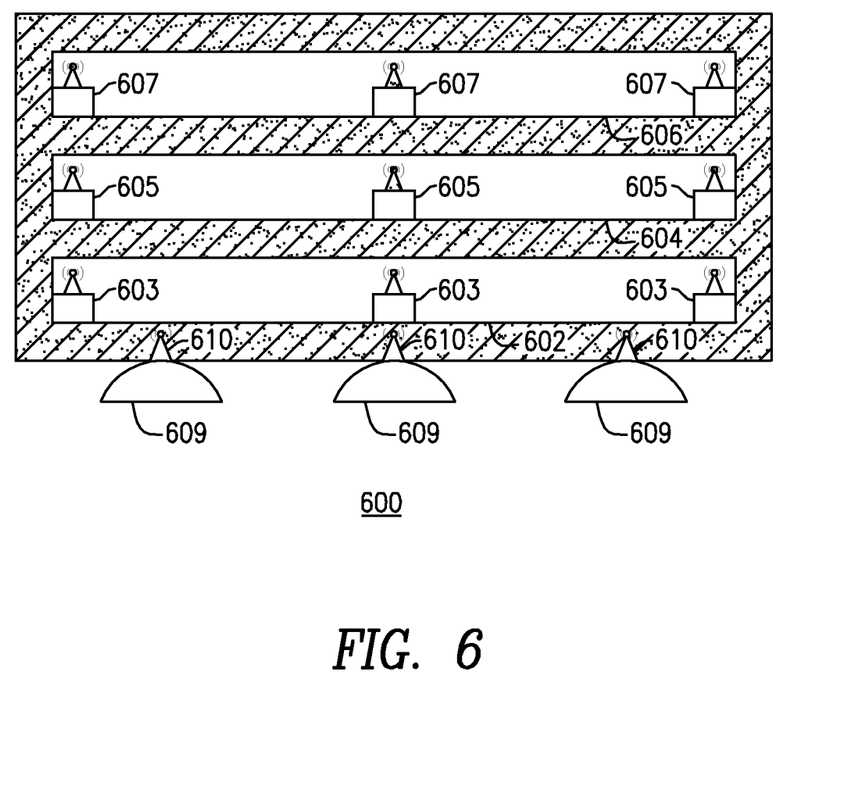
FIG. 6 shows yet another a sectioned view of an embodiment of a sponge according to the invention.

In still other embodiments of the invention, a sponge 600, may be equipped with RF (radio frequency) activated chambers 602, 604, and 606. Such chambers may preferably include ports 603, 605 and 607 that can be opened using a remote control signal. After ports 603, 605 and 607 are each opened (preferably at different times) the substance in each of the respective chambers may naturally be distributed throughout the sponge in order to reach substantially the entire wound.

In certain embodiments of the invention, chambers 602, 604, and 606 may be implemented as small bladders and distributed throughout the sponge. Such bladders may be held under pressure when the seal is applied to the sponge. Accordingly, in such an embodiment, when ports 603, 605, and 607 are opened, then the substance within the bladders may be quickly and efficiently distributed throughout the wound.

In yet another embodiment of the invention, ports 603, 605, and 607 may preferably be implemented using MEMS (micro-electric mechanical devices) valves. This embodiment of the MEMS valves is described in more detail below in the portion of the specification corresponding to FIGS. 9 and 10.

FIG. 6 also shows a number of lenses 609 that may also send optical signals in real-time relating to the appearance of the wound. Each of lenses 609 may be coupled either by wire or wirelessly through transmitters 610 to a display that may be provided to a health care provider. Such a display may provide the health care provider with an indication of the status of the wound and, accordingly, guide the health care provider in the implementation of commands to transmitters 607 which control the dispersion of the tissue digestive enzyme. It should be noted that lenses according to the invention may be used with any of the embodiments described herein unless specifically stated to the contrary. It should be understood that lenses 609 may, in certain embodiments of the invention, preferably be accompanied by a light source in order to allow viewing of the wound. Alternatively, the lens could be heat-responsive and provide a heat profile of the wound.

Figure 7:
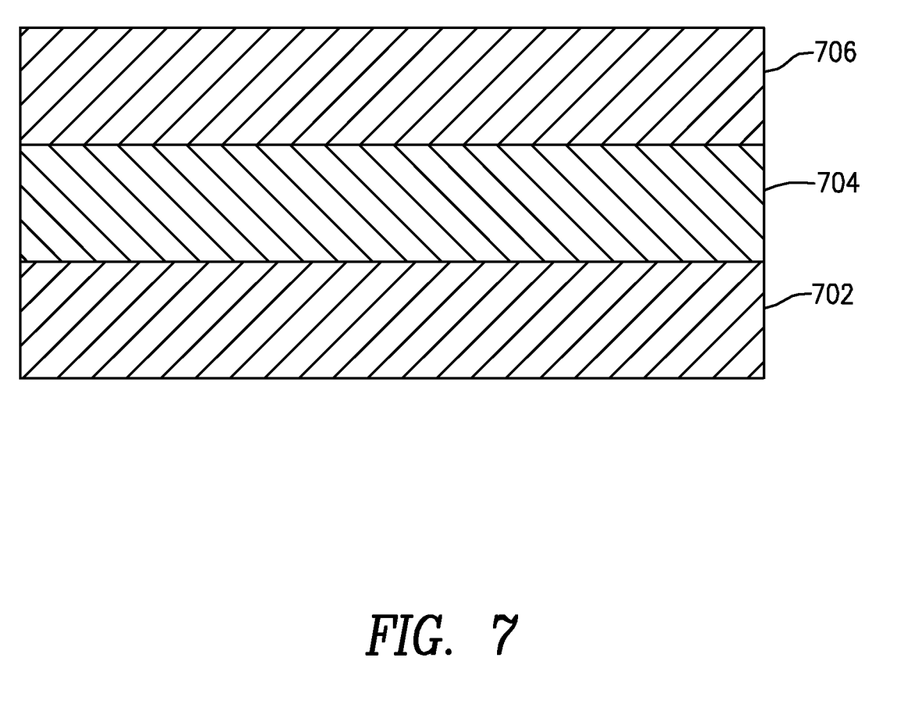
FIG. 7 shows still another section view of an embodiment of a sponge according to the invention.

FIG. 7 shows yet another embodiment of the invention, in which the sponge 700 itself is impregnated with the appropriate substance. Sponge 700 may preferably be formed from multiple layers 702, 704, and 706. Layer 702 may be impregnated with analgesic, layer 704 may be impregnated with antibiotic and layer 706 may be impregnated with a tissue digester. In such an embodiment, the sponge itself may form the layers of analgesic, antibiotic and tissue digester. Accordingly, sponge 700 may slowly dissolve and be taken up by the suction when applied.

In certain embodiments of sponge 700, different layers 702, 704 and 706 may be formed from different pore sizes and/or different materials. The different pore sizes and/or materials may serve to influence the wicking of substances dispersed in the sponge. For example, the lowest level of the sponge may be formed from the smallest pore size material which may enhance the dispersion of the substance in this portion of the sponge and, thereby, help facilitate the movement of the fluid to the portion of the sponge closest to the wound.

Figure 8:
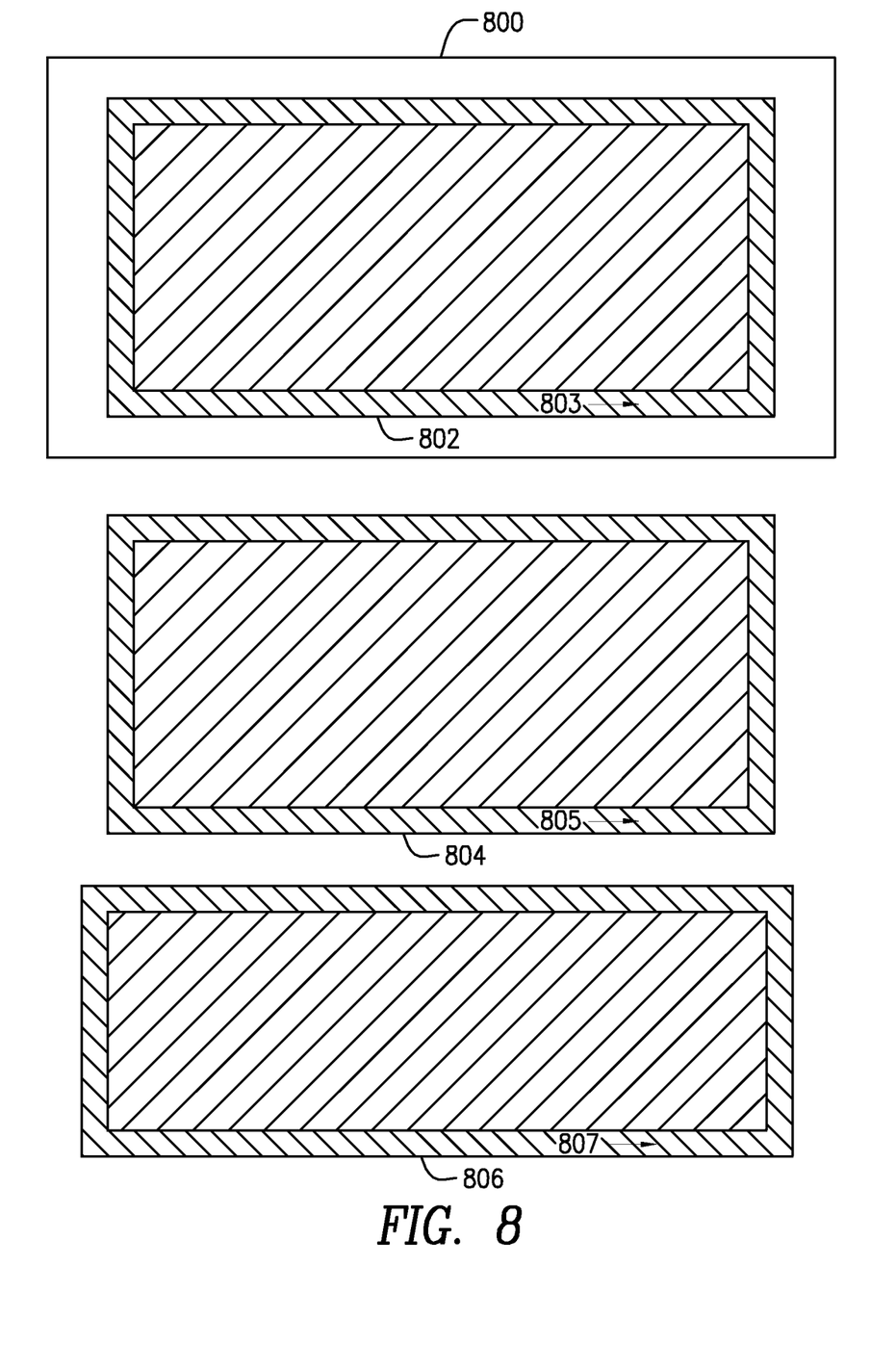
FIG. 8 shows a dressing for use with methods according to the invention.

In yet another embodiment of the invention, a dressing, such as a DuoDerm® dressing 800, or other suitable hydrocolloidal dressing, may be implemented with removable central pads 802, 804 and 806, such as those shown in FIG. 8. Each of pads 802, 804, and 806 may preferably include an outer edge 803, 805, and 807.

A DuoDerm® type pad 800, or some other suitable type of hydrocolloidal dressing, may be adhesively attached to the area around the wound. The outer edge 803, 805, and 807 of removable central pads 802, 804 and 806 may then be attached by VELCRO® or other suitable, preferably relatively less-bonding, removable connection to the underlying DuoDerm® pad 800. In such an embodiment of the invention, the removable portion of the pads can be changed without disengaging the adhesive connection of the DuoDerm® pad 800 to the area about the wound.

Each of such removable central pads 802, 804 and 806 pads can preferably be impregnated with a substance such as an analgesic, an antibiotic, and/or a tissue digester. In such an embodiment, a method according to the invention for treating a wound can be implemented using removable central pads 802, 804 and 806.

In another embodiment of the invention, the foam or sponge pad may also provided with an optical pigtail, as described in the above-incorporated '702 patent. This optical pigtail may include an optical fiber that has been formed to fan into a plurality of sections of the sponge. The fibers of the most distal fanned sections, which are implanted in the foam pad at its base, are provided with tiny optical slots. The optical slots may preferably be oriented toward the wound site.

Each optical slot can be made by stripping the cladding from the optical fiber in the certain areas of the fanned sections. Such slots form slot radiators. Each of the slot radiators may be adapted to illuminate a portion of the wound site.

It is often necessary to trim the foam pad in ordinary preparation for V.A.C. therapy wound treatment. Accordingly, the optical fibers preferably include plastic cores and claddings. Such cores and cladding may be appropriate for those wavelengths in the visible and near infrared spectrum as are typically utilized in phototherapy applications. One such material that can be employed for introduction of phototherapy into such a foam pad is acrylic. Acrylic is inexpensive and easy to cut. Other materials and adaptations may be utilized in alternative embodiments.

Figure 9:
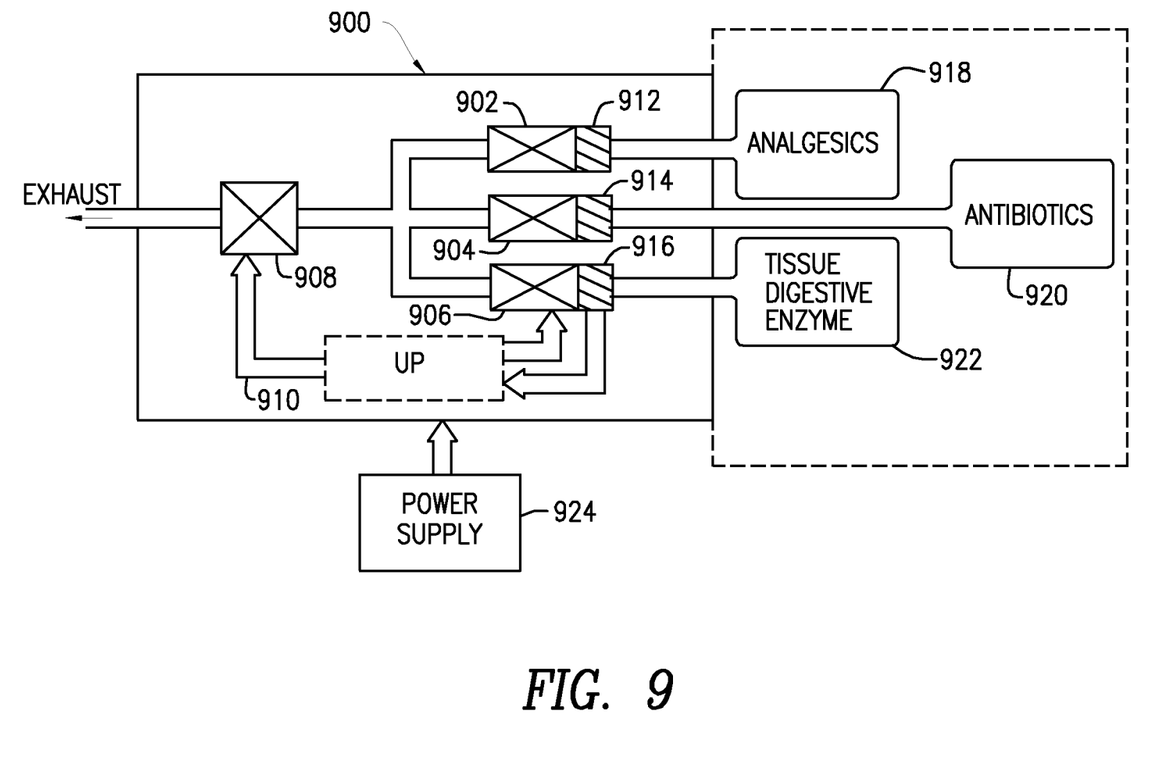
FIG. 9 shows a schematic diagram of an embodiment of a microelectrical mechanical system according to the invention.

FIG. 9 shows an embodiment of a microelectrical mechanical system (MEMS) 900 according to the invention. System 900 preferably includes valves 902, 904 and 906. Each of valves 902, 904 and 906 may control the flow from each of bladders 918, 920 and 922, respectively. System 900 may also include optional valve 908 which may further control the flow following the opening of one of valves 902, 904, and 906.

Certain embodiments of system 900 may include a microprocessor 910. Microprocessor 910 may control the operation of the valves either in response to pressure information received at one or more of pressure sensors 912, 914, and/or 916 (only the coupling of microprocessor 910 to sensor 916 is shown for the sake of clarity of the drawing) or from a remote source through wired or wireless communication.

It should be noted that each of valves 912, 914, and 916 may preferably be coupled to bladders 918, 920, and 922 such that the sensors detect the respective pressure from the bladders. Accordingly, one embodiment of the invention may comprise using check valves as valves 912, 914, and 916 which open in response to varying levels of pressure. Accordingly, valve 912 (which may be coupled to release analgesics) may open in response to a level of 115 millimeters Hg, valve 914 (which may be coupled to release antibiotics) may open in response to a level of 120 millimeters Hg, and valve 916 (which may be coupled to release a tissue digestive enzyme) may open in response to a level of 125 millimeters Hg. In this fashion, the various valves may be opened in a predetermined sequence by small increases in pressure without substantially affecting the efficacy or healing properties of the negative pressure.

One other distinct advantage that implementations of MEMS in the sponge may obtain is that the fluid-release devices may preferably be implemented with such small devices—e.g., on the order of between 1 and 50 millimeters—that the patient will not even notice the existence of the devices in the sponge nor will any deleterious effects be realized with respect to the wound.

Figure 10:
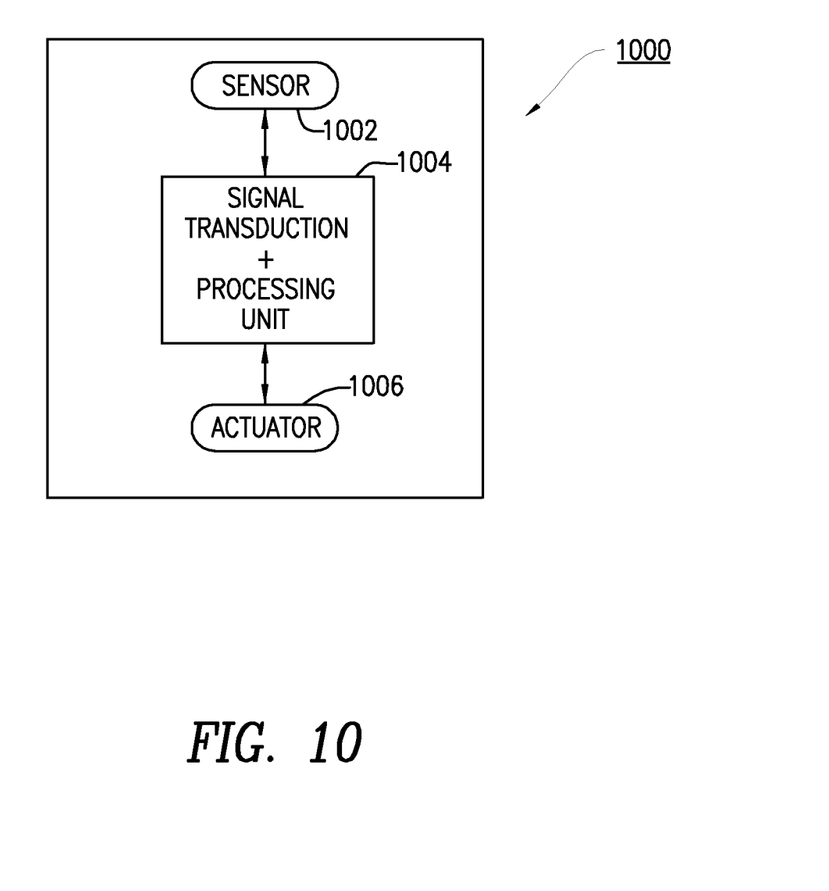
FIG. 10 shows a schematic diagram of a transducer that can be used in systems and methods according to the invention.

FIG. 10 shows one possible implementation of a single transducer 1000 that may be used in systems and methods according to the invention. Transducer 1000 may preferably include a sensor 1002 for determining certain environmental parameters such as pressure on the bladders which relates to the pressure being exerted on the sponge by the negative pressure device, a signal transduction and processing unit 1004 which receives information from the sensor. Finally signal transduction and processing unit 1004 may process the received information for controlling actuator 1006. Actuator 1006 may preferably form part of a valve or other relevant device that can be used to release fluid into the sponge.

Aspects of the invention have been described in terms of illustrative embodiments thereof. A person having ordinary skill in the art will appreciate that numerous additional embodiments, modifications, and variations may exist that remain within the scope and spirit of the appended claims. For example, one of ordinary skill in the art will appreciate that the steps illustrated in the figures may be performed in other than the recited order and that one or more steps illustrated may be optional.

Thus, systems and methods for providing a debriding wound vacuum have been described. Persons skilled in the art will appreciate that the present invention can be practiced by other than the described embodiments, which are presented for purposes of illustration rather than of limitation, and the present invention is limited only by the claims which follow.

What is claimed is:

1. A debriding wound vacuum for introducing a debridement substance to a wound located on a patient's body, the vacuum comprising:
    a source for introducing the debridement substance to the wound, wherein the source for introducing the debridement substance to the wound is external to the patient's body;
    a sponge for application to a wound, the sponge configured to receive a debridement substance from the source;

a negative pressure device for applying negative pressure to the wound;

a hollow tube for placing the negative pressure device in fluid communication with the sponge; and an optical feedback instrument to send optical signals in real time to a display to provide a health care provider with an indication of the status of the wound.

2. The debriding wound vacuum of claim 1, the sponge further comprising a time-release mechanism that releases the debridetnent substance at a predetermined time.

3. The debriding wound vacuum of claim 1 wherein the sponge is formed from a material that releases the debridement substance at a predetermined time.

4. The debriding wound vacuum of claim 1 wherein the sponge further comprises a chamber including the debridement substance.

5. The debriding wound vacuum of claim 4 further comprising a microelectronic mechanical valve for releasing the debridement substances from the chamber.

6. The debriding wound vacuum of claim 5, the microelectronic mechanical valve that comprises a receiver for receiving wireless signals.

7. The debriding wound vacuum of claim 1 wherein the sponge further comprises an elastic bladder including the debridement substance.

8. The debriding wound vacuum of claim 7 further comprising a microelectronic mechanical valve for releasing the debridement substances from the bladder.

9. The debriding wound vacuum of claim 1 wherein said debridement substance comprises introducing a tissue digesting enzyme.

10. The debriding wound vacuum of claim 1 wherein the debridement substance comprises collagenase.

11. A debriding wound vacuum for introducing a non-naturally occurring debridement substance to a wound located on a patient's body, the vacuum comprising:

a source for introducing the non-naturally occurring debridement substance to the wound, wherein the source for introducing the debridement substance to the wound is external to the patient's body;

a sponge for application to a wound, the sponge configured to receive a debridement substance from the source;

a negative pressure device for applying negative pressure to the wound;

a hollow tube for placing the negative pressure device in fluid communication with the sponge; and an optical feedback instrument to send optical signals in real time to a display to provide a health care provider with an indication of the status of the wound.

12. A debriding wound vacuum for introducing a non-wound-generated debridement substance to a wound located on a patient's body, the vacuum comprising:

a source for introducing the non-wound-generated debridement substance to the wound, wherein the source for introducing the debridement substance to the wound is external to the patient's body;

a sponge for application to a wound, the sponge configured to receive a debridement substance from the source;

a negative pressure device for applying negative pressure to the wound;

a hollow tube for placing the negative pressure device in fluid communication with the sponge; and an optical feedback instrument to send optical signals in real time to a display to provide a health care provider with an indication of the status of the wound.

13. A debriding wound vacuum for introducing a debridement substance to a wound located on a patient's body, the vacuum comprising:

a source for introducing the debridement substance to the wound, wherein the source for introducing the debridement substance to the wound is external to the patient's body;

a sponge for application to a wound, the sponge configured to receive a debridement substance from the source;

a negative pressure device for applying negative pressure to the wound;

a hollow tube for placing the negative pressure device in fluid communication with the sponge; and an optical feedback instrument to send optical signals in real time to a display to provide a health care provider with an indication of the status of the wound.

\* \* \* \* \*